United States Patent
Hällgren

(10) Patent No.: US 7,575,927 B2
(45) Date of Patent: Aug. 18, 2009

(54) METHODS FOR DIAGNOSING A GASTROINTESTINAL DISORDER IN AN INDIVIDUAL

(75) Inventor: Roger Hällgren, Bälinge (SE)

(73) Assignee: Alimenta Medical AB, Stockholm (SE)

( * ) Notice: Subject to any disclaimer, the term of this patent is extended or adjusted under 35 U.S.C. 154(b) by 80 days.

(21) Appl. No.: 11/900,067

(22) Filed: Sep. 10, 2007

(65) Prior Publication Data

US 2008/0064111 A1 Mar. 13, 2008

Related U.S. Application Data

(60) Provisional application No. 60/843,961, filed on Sep. 12, 2006.

(51) Int. Cl.
*G01N 33/48* (2006.01)
(52) U.S. Cl. .......................... 436/63; 436/86
(58) Field of Classification Search ................... 436/63, 436/86
See application file for complete search history.

(56) References Cited

U.S. PATENT DOCUMENTS 5,312,343 A * 5/1994 Krog et al. ............. 604/101.03
6,576,429 B1 * 6/2003 Hallgren ...................... 435/7.1

OTHER PUBLICATIONS

Deshpande et al. (abstract) European Journal of Pharmacology, vol. 256, issue 1, Apr. 11, 1994, pp. 1-2.*

Palsson, Olafur S., et al, "Elevated Vasoactive Intestinal Peptide Concentrations in Patients with Irritable Bowel Syndrome," Digestive Diseases and Sciences, Aug. 2004, vol. 49, No. 7/8, pp. 1236-1243.

Yamamoto, Hitoshi et al, "Abnormal Neuropeptide Concentration in Rectal Mucosa of Patients With Inflammatory Bowel Disease," J. Gastrointestinal, 1996, vol. 31, pp. 525-532.

Coates, Matthew D., et al, "Molecular Defects in Mucosal Serotonin Content and Decreased Serotonin Reuptake Transporter in Ulcerative Colitis and Irritable Bowel Syndrome," Gastroenterology, 2004; 126:1657-1684/.

Kristjansson, G. et al, "Clinical and Subclinical Intestinal Inflammation Assessed By the Mucosal Patch Technique: Studies of Mucosal Neutrophil Disease and Irritable Bowel Syndrome," Gut. 2004, vol. 53, pp. 1806-1812.

Carlson, M. et al, "Increased Intraluminal Release of Eosinophil Granule Proteins EPO, ECP, EPX and Cytokines in Ulcerative Colitis and Proctitis in Segmental Perfusion," The American Journal of Gastroenterology, 1989, vol. 94, No. 7, pp. 1876-1883.

* cited by examiner

*Primary Examiner*—Maureen M Wallenhorst
(74) *Attorney, Agent, or Firm*—Porter Wright Morris & Arthur LLP

(57) ABSTRACT

Methods for measuring at least one mucosally released neuroendocrine gut system component in an individual and methods for diagnosing a gastrointestinal disorder in an individual based on the concentration of at least one mucosally released neuroendocrine gut system component, and/or the ratio of the concentrations of at least one mucosally released neuroendocrine gut system component and at least one mucosally released inflammatory release mediator are provided.

24 Claims, 6 Drawing Sheets

METHODS FOR DIAGNOSING A GASTROINTESTINAL DISORDER IN AN INDIVIDUAL

RELATED APPLICATION

The present application claims the benefit under 35 U.S.C. §119 of U.S. Application Ser. No. 60/843,961 filed Sep. 12, 2006.

FIELD OF THE INVENTION

The present invention relates to methods for measuring at least one mucosally released neuroendocrine gut system component. The present invention also relates to methods for diagnosing a gastrointestinal disorder in an individual based on the concentration of at least one mucosally released neuroendocrine gut system component and/or the ratio of the concentrations of at least one mucosally released neuroendocrine gut system component and at least one mucosally released inflammatory release mediator.

BACKGROUND OF THE INVENTION

Irritable bowel syndrome (IBS) is a highly prevalent functional disorder characterized by the presence of abdominal pain and discomfort and changes in bowel habits (diarrhea and/or constipation) in the absence of reliable biological markers. IBS represents a spectrum of conditions with dysregulation of visceral function and afferent sensation and an association to emotional factors and stress. This syndrome has been viewed as a disorder of the brain-gut axis but recently roles for enteric infection and intestinal inflammation have also been proposed. Ulcerative colitis (UC) shares the symptoms of IBS but is, in contrast to IBS, an obvious inflammatory mucosal disease of the colon. The insight that molecular crosstalk exists between immune, nervous and neuroendocrine systems has widened the perspective of the pathophysiology of inflammatory attacks on various organs, including the gut.

The nervous and immune systems have a common language based on small molecules-cytokines and neuro-transmitters/peptides. The enteric nervous system (ENS) is largely an independent system and its reflexes may work independent of brain influences. However, no nerves enter the gut epithelium and luminal stimuli must therefore be detected and translated to nerves by neuro-transmitters/peptides released by enterochromaffin (EC) cells. The EC cells store huge amounts of various neuropeptides and are in fact the largest endocrine organ in the body. Neuro-transmitters/peptides are co-stored with chromogranins, a family of granule-specific, water-soluble acidic proteins. This family comprises five members and among them chromogranin A (CGA) and chromogranin B (CGB) are the most frequent granins localized in secretory organelles of endocrine cells and neurons. Intracellular CGA and CGB might play central roles in the secretory process partly by acting as helper proteins in the packaging of peptides, hormones or neuropeptides.

In an attempt to elucidate the involvement of neurotransmitters/peptides in inflammatory bowel diseases (IBD) and functional bowel disorders like irritable bowel syndrome (IBS), clinical studies have been based on plasma measurements, immunohistochemistry or quantitation of the content of neuropeptides in mucosal biopsies. However, many of the results obtained have been conflicting. The lack of easily accessible methods to assess the involvement of neuropeptides in UC and IBD has hampered the clinical insight of the role neuropeptides may play in these conditions.

SUMMARY OF THE INVENTION

The present invention provides methods for measuring at least one neuroendocrine gut system component in an individual. The methods comprise measuring at least one neuroendocrine gut system component from the individual. The at least one neuroendocrine gut system component is mucosally released.

The present invention also provides methods for diagnosing a gastrointestinal disorder in an individual. The methods comprise measuring at least one neuroendocrine gut system component of the individual, calculating the concentration of the at least one neuroendocrine gut system component and diagnosing the gastrointestinal disorder in the individual based on the concentration of the at least one neuroendocrine gut system component. The at least one neuroendocrine gut system component is mucosally released.

The present invention further provides methods for diagnosing a gastrointestinal disorder in an individual. The methods comprise measuring at least one neuroendocrine gut system component and at least one release inflammatory mediator of the individual, calculating the concentrations of the at least one neuroendocrine gut system component and the at least one release inflammatory mediator, determining a ratio of the concentrations of the at least one neuroendocrine gut system component and the at least one release inflammatory mediator, and diagnosing the gastrointestinal disorder in the individual based on the ratio of the concentrations of the at least one neuroendocrine gut system component and the least one release inflammatory mediator. The at least one neuroendocrine gut system component and/or the at least one release inflammatory mediator are mucosally released.

BRIEF DESCRIPTION OF THE DRAWINGS

The following Detailed Description may be more fully understood in view of the drawings, in which.

DETAILED DESCRIPTION OF THE INVENTION

Figure 1A:
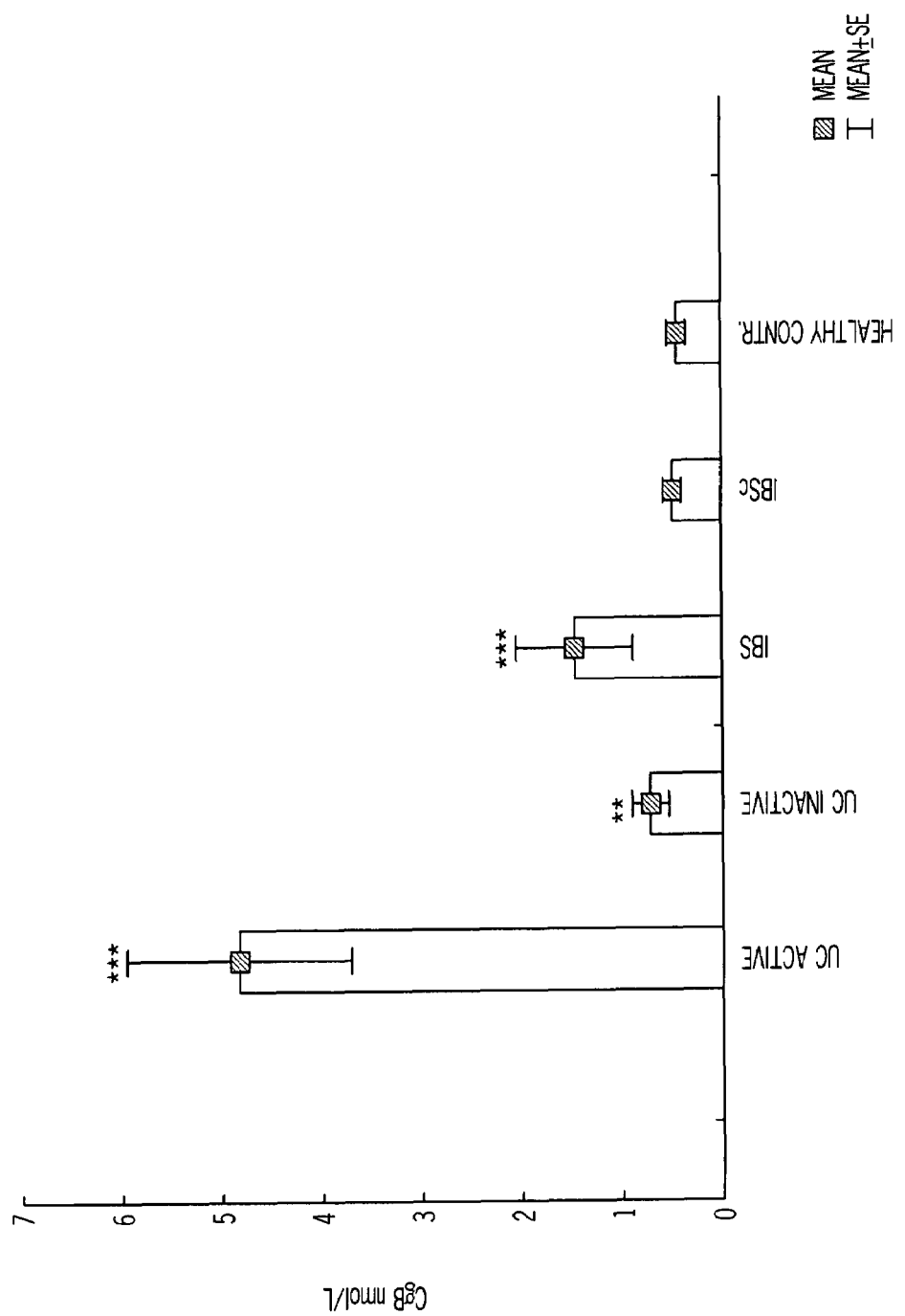
FIGS. 1A and 1B illustrate the rectal luminal release of CGB and CGA in individuals with active/inactive ulcerative colitis (UC), in individuals with irritable bowel disease of diarrhea-predominant or alternating types (IBS) or constipation (IBSc) and in healthy individuals. Statistical comparisons (Mann-Whitney U-test) with the individuals are indicated: * p<0.05,  p<0.01, * p<0.001.

The inventor has determined that neuroendocrine gut system components are released into the colon and/or rectal lumen and appear in increased concentrations if the individual has a gastrointestinal disorder. Accordingly, the inventor has determined methods for measuring at least one neuroendocrine gut system component in an individual. In one embodiment, the methods comprise measuring at least one neuroendocrine gut system component from the individual. The at least one neuroendocrine gut system component is mucosally released.

The inventor has also determined methods for diagnosing a gastrointestinal disorder in an individual. In one embodiment, the methods comprise: measuring at least one neuroendocrine gut system component of the individual, calculating the concentration of the at least one neuroendocrine gut system component and diagnosing the gastrointestinal disorder in the individual based on the concentration of the at least one neuroendocrine gut system component. The at least one neuroendocrine gut system component is mucosally released.

One skilled in the art will appreciate the various types of gastrointestinal disorders that may be diagnosed by the present methods. Gastrointestinal disorders that may be diagnosed by the present methods comprise an inflammatory gastrointestinal disorder, a functional gastrointestinal disorder, or a combination of gastrointestinal disorders. Examples of an inflammatory gastrointestinal disorder include, but are not limited to, ulcerative colitis, Crohn's disease or a combination thereof. An example of a functional gastrointestinal disorder includes, but is not limited to, irritable bowel disease.

One skilled in the art will also appreciate the various mucosally released neuroendocrine gut system components that may be measured, any of which may be measured herein. Examples of mucosally released neuroendocrine gut system components include, but are not limited to, neurohormones, neuropeptides, endogenous opiods, neurotransmitters or combinations thereof. Examples of neurohormones include, but are not limited to, chromogranin A, chromogranin B or a combination thereof. Examples of neuropeptides include, but not limited to, CRH, Substance P, peptide YY (PYY), vasoacitve intestinal peptide (VIP), or a combination thereof. Examples of neurotransmitters include, but not limited to, serotonin, adrenalin, non-adrenaline or a combination thereof.

One skilled in the art will also appreciate the methods that may be used to measure the mucosally released neuroendocrine gut system component(s) in the individual, any of which may be employed herein. Such measurement techniques include, but are not limited to, mucosal patch technique, perfusion of the colon and/or rectum, dialysis of the colon and/or rectum, analysis of fecal content, or a combination thereof. The mucosal patch technique, as described by Kristjansson et al, "Clinical and subclinical intestinal inflammation assessed by the mucosal patch technique: studies of mucosal neutrophil and eosinophil activation in inflammatory bowel diseases and irritable bowel syndrome." Gut 2004; 53 (12): 1806-12, is based on the principal that filter paper attached to balloons, and thereby compressed against the rectal and/or colon mucosa of an individual, absorb neuroendocrine gut system component(s) that are released to the lumen from the mucosa. The absorbed neuroendocrine gut system component(s) can then be measured to determine their concentration. The absorbed neuroendocrine gut system component(s) are then extracted from the filter paper (patch) by a defined volume of extraction fluid and measured to determine their concentrations. The concentrations of mucosally released inflammatory mediator(s) are calculated in the same way.

The inventor has determined that the gastrointestinal disorder of the individual can be diagnosed based on the concentration of at least one mucosally released neuroendocrine gut system component. In one embodiment, an increase in the concentration of the mucosally released CRH above 2 ug/L, the individual will be diagnosed with a gastrointestinal disorder.

The inventor has also determined that certain gastrointestinal disorders are inflammatory active mucosal diseases. Accordingly, in a further embodiment, the inventor has determined methods of diagnosing a gastrointestinal disorder in an individual comprising: measuring at least one neuroendocrine gut system component and at least one release inflammatory mediator of the individual, calculating the concentrations of the at least one neuroendocrine gut system component and the at least one release inflammatory mediator, determining a ratio of the concentrations of the at least one neuroendocrine gut system component and the at least one release inflammatory mediator, and diagnosing the gastrointestinal disorder in the individual based on the ratio of the concentrations of the at least one neuroendocrine gut system components and the least one release inflammatory mediator. The at least one neuroendocrine gut system component and/or the at least one release inflammatory mediator are mucosally released.

One skilled in the art will appreciate the various mucosally released inflammatory mediators that may be measured, any of which may be employed herein. Examples of inflammatory mediators include, but are not limited to, proinflammatory cytokines, and granule constituents from macrophages, granulocytes or basophils/mast cells or combinations thereof.

The inventor has determined that the gastrointestinal disorder of the individual can be diagnosed based on the ratio of the concentrations of the at least one mucosally released neuroendocrine gut system component and the least one mucosally release inflammatory release mediator. In one embodiment, if the ratio value of CRH (ng/L): IL-6 is less than about 200 than the individual is diagnosed with ulcerative colitis. In yet another embodiment, if the ratio value of CRH (ng/L): ILH-6 is greater than about 250 than the individual is diagnosed with IBS, diarrhea-predominant or alternative types. In yet another embodiment, if the ratio value of CgA (nmol/l):MPO (ug/L) is less than about 15 than the individual is diagnosed with ulcerative colitis. In another embodiment, if the ratio value of CgA (nmol/l):MPO (ug/L) is greater than about 20 than the individual is diagnosed with IBS, diarrhea-predominant or alternative types.

EXAMPLES

Example 1

Luminal Release of Chromogranins and Neuropeptides as Biological Markers for Irritable Bowel Syndrome and Ulcerative Colitis It has been determined that individuals with UC or diarrhea-dominating IBS had a conspicuous intraluminal release of Chromogranin A and B (CgA and CgB), commonly viewed as markers for endocrine and neuronal cells. This observation induced the inventor to also study the possible co-release of corticotropin releasing hormone (CRH) and substance P, neuropeptides that have been discussed in the pathogenesis of UC and IBS. Finally, the chromogranin findings are related to the mucosal inflammatory activity.

Subjects and Methods

Individuals with UC (n=25), IBS (n=13) and healthy individuals (n=15) underwent investigation of the rectal mucosa by using the mucosal patch technique by which filter paper being compressed against the mucosa absorb mediators released to gut lumen from the mucosa. Chromogranin A and B (CgA and CgB), corticotropin releasing hormone (CRH) and substance P are measured as well as proinflammatory cytokines.

Subjects

Healthy individuals (n=17, M/F=12/5, mean age 30 years, range 19-58) and individuals with functional and inflammatory bowel diseases are studied at the Section of Gastroenterology at the University Hospital of Uppsala. The groups include: A. Individuals with irritable bowel syndrome (IBS) of diarrhea-predominant or alternating types (n=13, M/F=11/2, mean age 39 years, range 22-61) and constipating type (n=8, M/F=7/1, mean age 52 years, range 33-68) B. Individuals with ulcerative colitis (UC; n=27, M/F=18/7,mean age 44.7 years, range 19-79) C. Individuals with coeliac disease (n=10, M/F=5/5, mean age 51 years, range 25-68) and individuals with collagen colitis (n=9, M/F=0/9, mean age 50 years, range 33-80). The IBS individuals fulfilled the ROME II criteria. Diagnosis of UC is based on clinical and endoscopic criteria and X-ray of the gut. Diagnosis of collagen colitis is based on clinical symptoms and colonic biopsy. Individuals with coeliac disease are diagnosed on duodenal biopsies showing regression or normalisation of the duodenum after a gluten-free diet. Individuals and healthy individuals are prepared as for routine fibresigmoidoscopy, with a non-irritative hyperosmolar sorbitol rectal enema (Klyx; Ferring, Malmö, Sweden).

Mucosal Patch Technique

The individuals and healthy individuals are investigated by the mucosal patch technique. The technique is based on the principle that filter paper attached to an inflatable balloon is compressed against the rectal mucosa. The patches absorb mediators released from the mucosa. After the investigation mediators are extracted from the patches and analysed. The extracts are after centrifugation immediately frozen in $-70°$ C. and kept frozen until analysis in sequence are performed.

Analytical Measurements

Figure 1B:
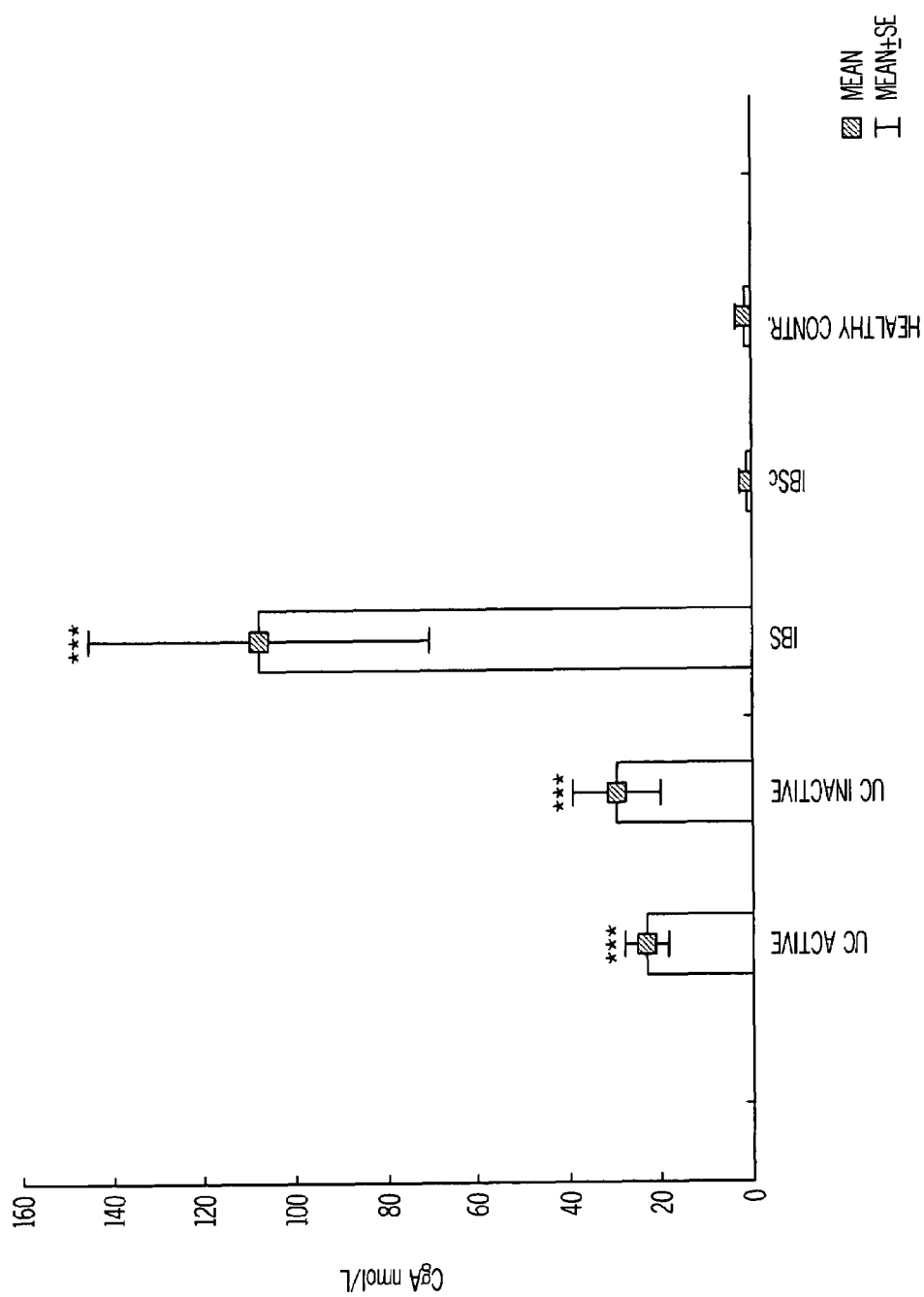
Figure 2:
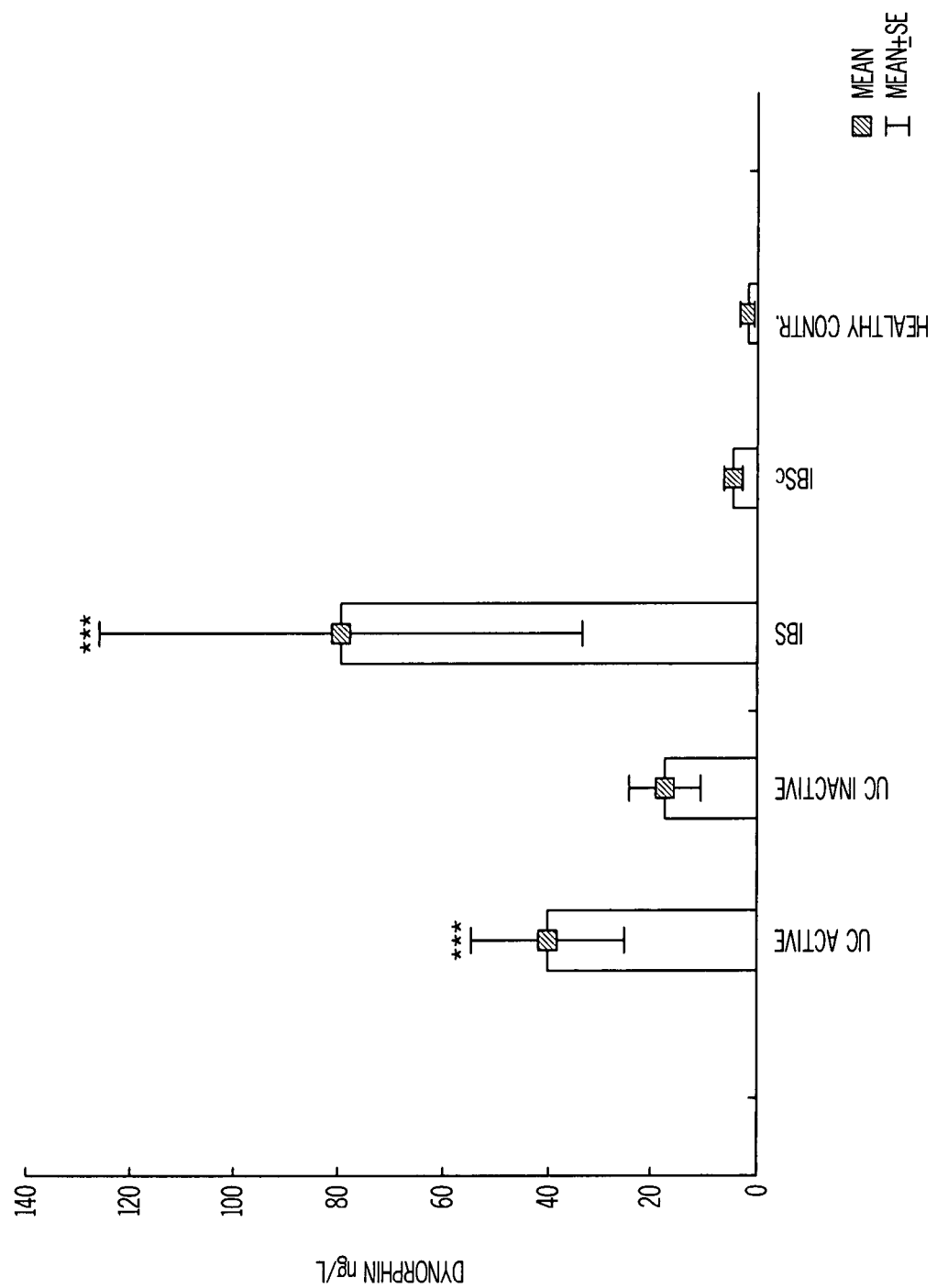
FIGS. 2-5 illustrate the rectal mucosal release of beta-endorphin, endomorphin, met-enkephalin and dynorphin in individuals with active/inactive ulcerative colitis (UC), in individuals with irritable bowel disease of diarrhea-predominant or alternating types (IBS) or constipation (IBSc), and in healthy individuals. Statistical comparisons with the individuals using Mann-Whitney U-test are illustrated by symbols; * p<0.05,  p<0.01,* p<0.001.
Figure 3:
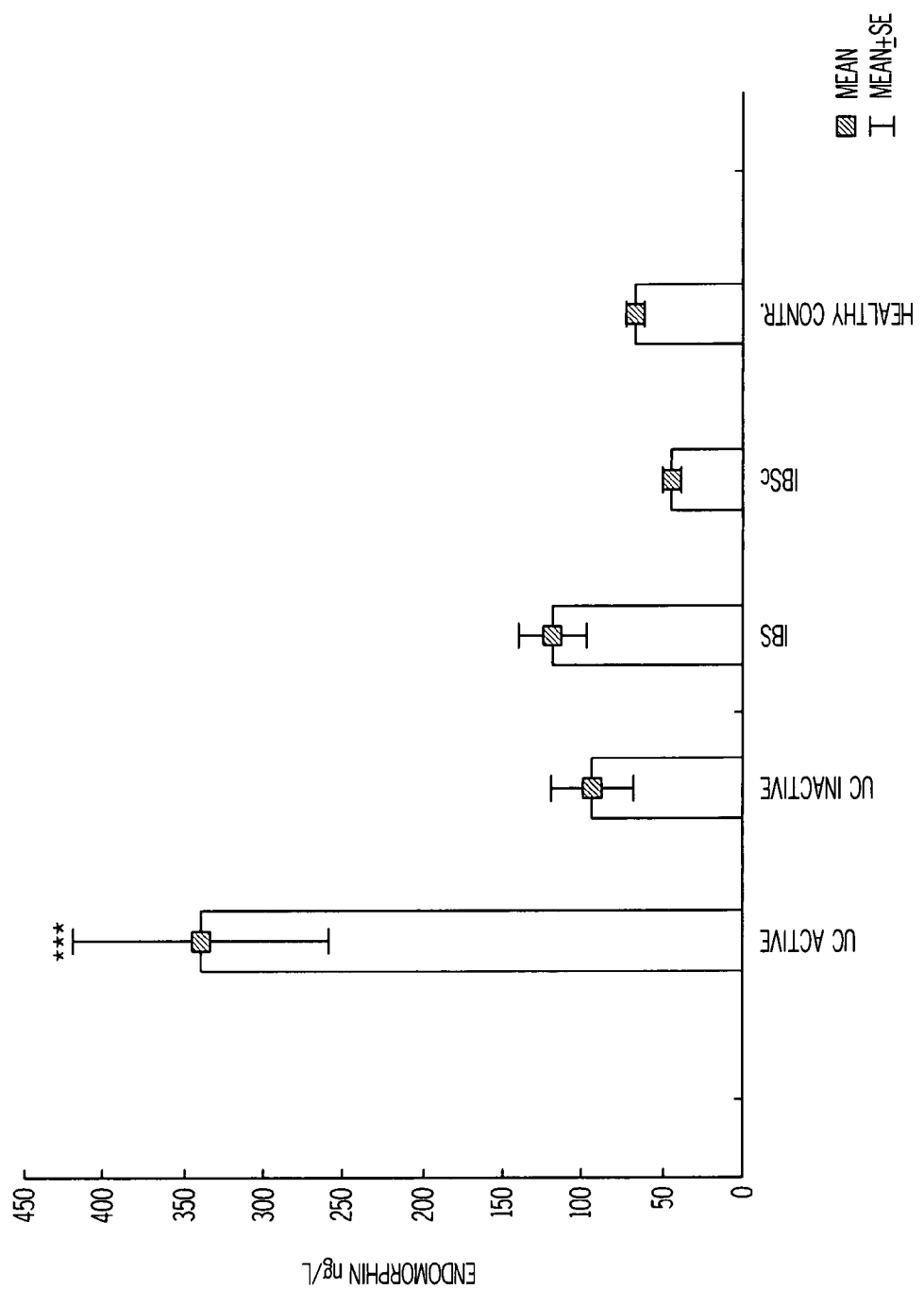
Figure 4:
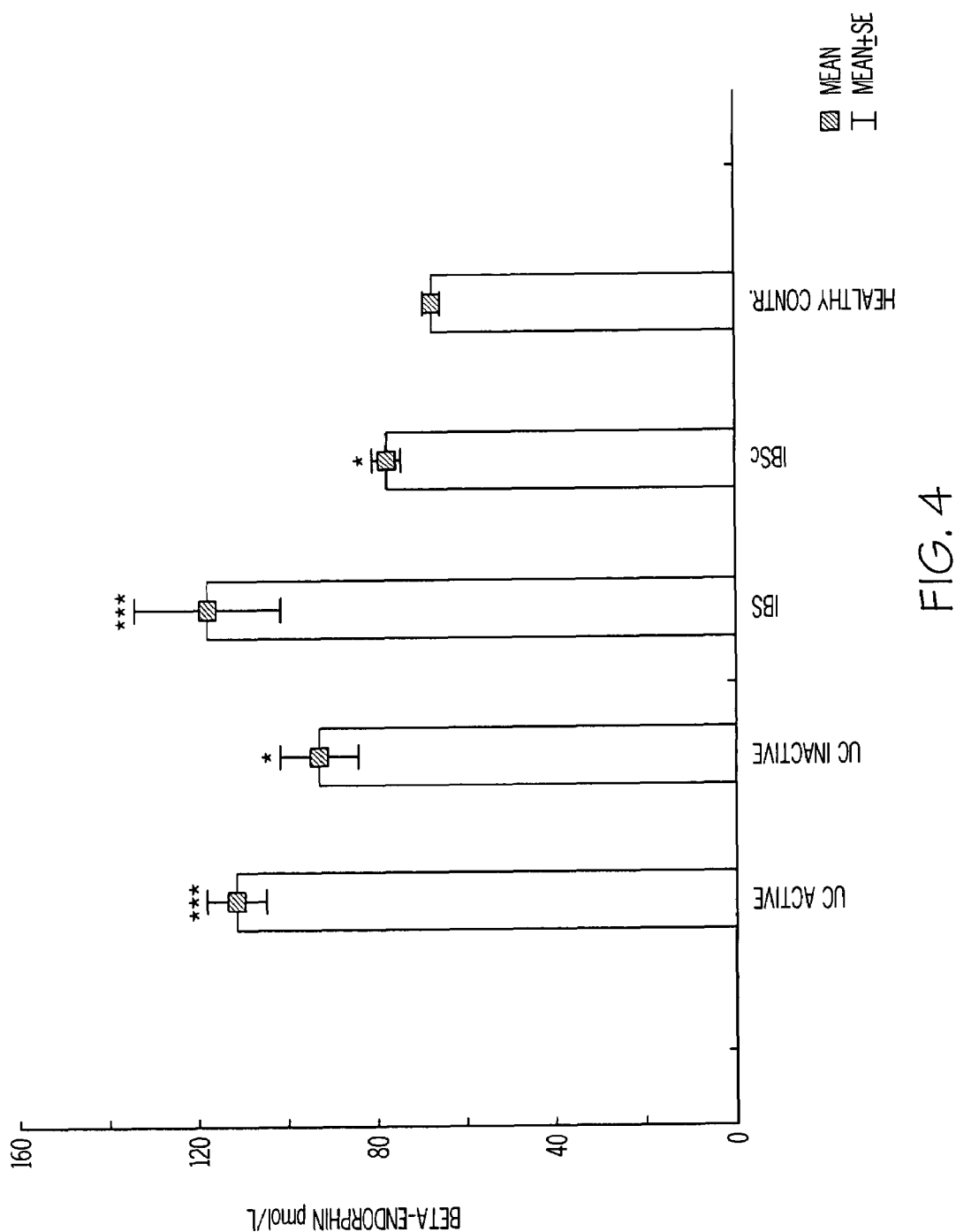
Figure 5:
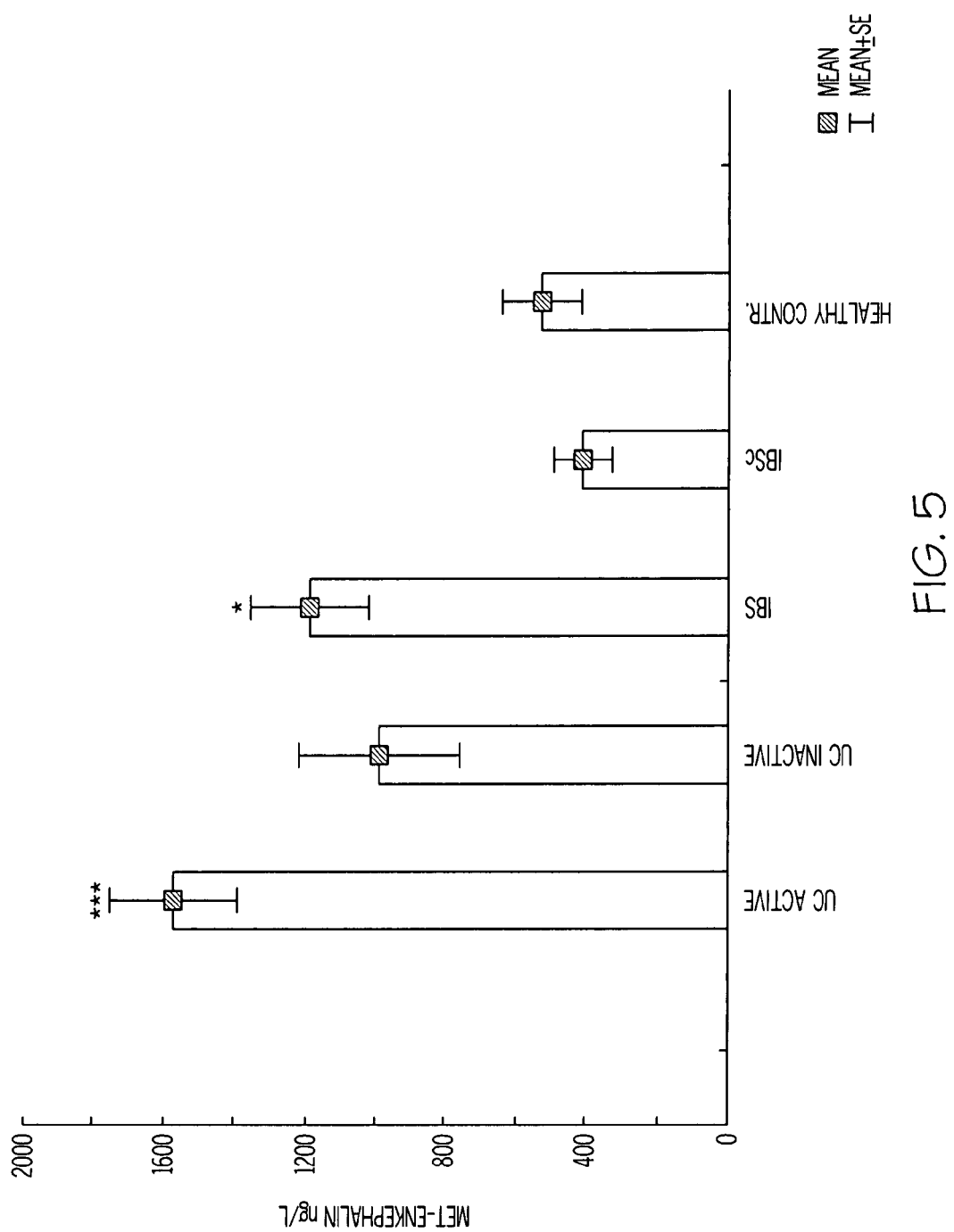

Chromogranin A (CGA) and chromogranin B (CGB) are measured using radioimmunoassays. Various cytokines amounts of CGA and CGB (FIG. 1). All individuals and healthy individuals have the same low circulating levels of chromogranins.

The released pattern of chromogranins are further analysed with respect to mucosal inflammation in individuals with UC and IBS. No abnormalities of the gut mucosal structure are seen in IBS while individuals with UC had varying degree of mucosal inflammation. The clinical grading of the activity of UC uses a four-graded endoscopic scale where score 1 represents normal mucosa and score 4 is a mucosa with pronounced granularity and fragility together with ulcerations. Individuals with active UC (n=26) have considerably increased CGB values compared to healthy individuals and individuals with IBS. Those UC individuals with inactive disease (n=8) have almost normalized their CGB values. The highest CGA values are found in individuals with IBS and disease activity score have no influence of the CGA values in UC (FIG. 1).

A number of pro-inflammatory cytokines released to lumen are analysed in individuals with UC and IBS in order to further characterize the inflammatory reaction. The data are summarized in Table 1. The strong release of TNF-alfa, IL-6, interferon-gamma and in particular IL-8 in active UC is obvious. Individuals with clinically inactive UC have much lower levels but still significant increases of these cytokines compared to the individuals. Individuals with IBS have increased levels of IL-8 and interferon-gamma suggesting a low-degree inflammatory reaction. Released CGB in UC individuals correlated significantly (p<0.01: Spearman rank order correlation test) with released amounts of TNF-alfa (r=0.54), IL-2 (r=0.58), IL-6 (r=0.65) and interferon-gamma (r=0.56) demonstrating that CGB is part of the inflammatory reaction in this disease. In contrast, CGA is not related to any of the measured cytokines. Released chromogranins in IBS are not correlated with cytokines.

TABLE 1

Luminal release of pro-inflammatory cytokines in individuals with active and inactive ulcerative colitis and in individuals with irritable bowel syndrome of diarrhea-predominant or alternating types.

| Diagnosis | TNF-alfa (ng/L) | IL-2 (ng/L) | IL-6 (ng/L) | IL-8 (ng/L) | Interferon-.gamma (ng/L) |
|---|---|---|---|---|---|
| Ulcerative colitis active | 14.4 + 4.7*** | 3.0 + 0.7** | 27 + 9.5*** | 1757 + 622*** | 33 + 10.8*** |
| Ulcerative colitis inactive | 2.5 + 0.7** | 1.6 + 0.6 | 4.3 + 1.7* | 57 + 2* | 12.3 + 5.2** |
| IBS | <1.5 | <1.0 | <1.0 | 25 + 8 | 2.6 + 0.4** |
| Healthy individuals | <1.5 | <1.0 | <1.0 | 13 + 2.2 | 1.6 + 0.4 |

The values are means + SE. Compared to healthy individuals (Mann-Whitney U test):
*p < 0.05,
**p < 0.01,
***p < 0.001

(TNF-alfa, IL-2, IL-6, IL-8 and interferon-gamma) are measured using Bio-Plex amine coupling kit and analysed with Bio-plex protein array system (Bio-Rad Laboratories, INC, Hercules, Calif., USA)

Results

Healthy individuals as well as individuals with coeliac disease and collagen colitis release very low levels of CGB and CGA. Increased release of these chromogranins is seen in individuals with ulcerative colitis and individuals with IBS diarrhea -predominant or alternating types. Individuals with IBS and constipation release like healthy individuals minimal Finally, the luminal release of two neuropeptides, substance-P and CRH are measured in order to elucidate whether or not these neuropeptides are released in parallel with a chromogranin release. The neuropeptide values are presented in Table 2. The large amount of released CRH in relation to released Substance P is obvious. Substance P and CRH are increased to the same extent in active or inactive UC. The highest values of substance P and CRH are noted in IBS of diarrhea-predominant or alternating types (Table 2). In individuals with UC significant correlations are found between Substance P and CGB and between CRH and CGA (Table 3). In IBS individuals the release of Substance P is significantly correlated with CGB as well as CGA (Table 3). In IBS, strong correlations between CRH and CGB and CGA are also determined (Table 3).

TABLE 2

The luminal release of Substance P and CRH in individuals with active and inactive ulcerative colitis and in individuals with irritable bowel syndrome of diarrhea-predominant or alternating types

| Diagnosis | Substance P (ng/L) | CRH (ug/L) |
|---|---|---|
| Ulcerative colitis, active | 3.7 + 0.2*** | 2.81 + 0.35*** |
| Ulcerative colitis, Inactive | 3.2 + 0.4* | 5.49 + 2.05* |
| IBS | 4.5 + 0.6*** | 16.88 + 7.23 |
| Healthy individuals | 2.4 + 0.1 | 1.68 + 0.07 |

The values are means + SE. Compared to healthy individuals (Mann-Whitney U-test):
*$p < 0.05$,
**$p < 0.01$,
***$p < 0.001$

TABLE 3

Correlations between mucosal release of CGB/CGB and the luminal release of Substance P and CRH in individuals with ulcerative colitis and individuals with IBS with diarrhea-predominant or alternating types

| | Substance P r | CRH r |
|---|---|---|
| A. Ulcerative colitis | | |
| CGB | 0.64** | ns |
| CGA | ns | 0.76*** |
| B. IBS | | |
| CGB | 0.81*** | 0.86** |
| CGA | 0.71*** | 0.72*** |

Correlation coefficients (r) were calculated using Spearman rank order correlation test;
**$p < 0.01$,
***$p < 0.001$

| | | |
|---|---|---|
| IBS | 4.5 + 0.5** | 16.88 + 7.23***. |
| Healthy individuals | 2.4 + 0.1 | 1.58 + 0.07 |

The values are means + SE. Compared to healthy individuals (Mann Whitney U-test);
*$p < 0.05$,
**$p < 0.01$,
***$p < 0.001$ Discussion The present example shows that chromogranins may be released into rectal lumen. Intraluminal release of CgA and CgB is not present in healthy individuals or disease individuals like celiac disease or collagen colitis but quite obvious in individuals with UC and in individuals with IBS with symptoms of diarrhea or alternating constipation and diarrhea but not in IBS individuals with constipation.

Chromogranins have dual function, as proteins for hormone storage and granulogenesis, and as prohormone for regulatory peptides. Several of the CGA and CGB-derived peptides are inhibitory to microbial and fungal growth implicating the chromogranins in defence reactions against various pathogens possibly primarily or secondarily involved in UC and IBS. Chromogranins are stored in rather high concentrations in large dense core secretory granules of most endocrine and neuroendocrine cells and in many nerve cells in periphery and brain. These secretory granules are the storage organelles of the regulated secretory pathway of neuroendocrine cells and chromogranins have been defined as marker proteins for these organelles. The chromogranins are normally present in low nanomolar concentrations in the circulation but appear in high concentrations in individuals with neuroendocrine tumours. The individuals in the present example with UC or IBS do not have elevated blood concentrations of measured chromogranins implicating that the mucosal release of CGB and CGA are local mucosal events and that the major mucosal release of granins are directed to the gut lumen and not to the circulation.

While not wishing to be bound by theory, the inventor believes that available data in the present example suggest certain possible stimulatory pathways. One observation of potential interest is the relations seen between the measured chromogranins and various variable reflecting degree of mucosal inflammation in UC. The CGA release is similar in subjects with active disease or disease in remission. In contrast, the CGB release is apparent only in active disease and is also related to the histological activity score as well as to the mucosal enhanced release of proinflammatory cytokines (TNF-alfa, IL-6, IL-8 and interferon-gamma). These cytokines have previously been demonstrated in the colonic mucosa of UC individuals by other techniques than the mucosal patch technique and are suitable as markers of mucosal inflammation since they all seem relevant to the mucosal damage seen in UC. The luminal release pattern of chromogranins implicates that at least the enhanced CGB release is part of the inflammatory reaction in UC. In fact, RNA—messengers coding for CGB—but not CGA—has recently been identified in human monocytes suggesting that CGB to some extent may have immune origins.

The individuals with IBS had no structural mucosal changes but had marginally elevated mucosal release of some cytokines (IL-8 and interferon-gamma), another finding supporting previous observations of subclinical inflammation in IBS. However, the inventor finds it not likely that the observed enhanced mucosal release of CGB as well as CGA in IBS is secondary to an inflammatory reaction. While not wishing to be bound by theory, the inventor proposes that the mucosal release of chromogranins in IBS is of neuronal origin or linked to or induced by enhanced local sympathetic/parasympathetic activity.

An enhanced release of corticotropin releasing hormone (CRH) as well as substance P in the subjects with IBS and UC has also been determined. These neuropeptides have been found in increased mucosal amounts at least in UC and their biological activities are proposed to be involved in mucosal inflammatory reactions and gut motility dysfunction. The large amounts of mucosal CRH are intriguing, suggesting that CRH in particular may be of pathophysiological relevance. CRH may act as a pro-inflammatory cytokine in UC by enhancing but not inducing a mucosal inflammatory reaction. Since CRH seems to have minimal stimulatory effect on unstimulated immunocytes, its primary effect in IBS might be to increase the colonic motility by increasing colonic intraluminal pressure.

The substance P released amounts covaried with released CGB in UC and are strongly related to both CGB and CGA in individuals with IBS. A correlation to released CRH is seen for CGA but not for CGB in UC and strong correlations were seen between CRH and both CGA and CGB in IBS. This pattern of co-variance/lack of co-variance may suggest that substance P and CRH are stored in heterogeneous chromogranin-expressing cells which may differ between these two diseases.

Irrespective of the mechanisms and the cellular origin of the mucosal CGA and CGB observed in UC and IBS, the example clearly demonstrates that chromogranins as well as specific neuropeptides are luminally released. This knowledge is of clinical value in the characterization of different subgroups of IBS and in therapeutic follow-studies in individuals with UC as well as IBS.

Example 2

Enhanced Rectal Mucosal Secretion of Endogenous Opioids in Irritable Bowel Syndrome and Ulcerative Colitis; Relationship to Local Production of CRH and IL-1

In this example, the luminal rectal release of endogenous opioids in individuals with IBS compared to healthy individuals and individuals with UC is studied. Endogenous opioids are schematically divided into three different classes of active peptides (enkephalins, dynorphins, and endorphins/endomorphins. An enhanced luminal secretion of such opioids in IBS as well as in UC has been determined. Since the biological activities of opioids include not only modulation of pain and mucosal secretion of electrolytes and absorption of water but also immunoregulation, these findings may contribute to the pathophysiological understanding of especially IBS, a heterogeneous syndrome suffering from the absence of biological markers. In order to elucidate some possible mechanisms behind the luminal release of opioids, the luminal secretion of IL-1 and CRH (corticotropin releasing hormone), which both are reported to produce release of endogenous opioids, is also measured.

Subjects and Methods

Subjects

Individuals with ulcerative colitis (UC), irritable bowel syndrome (IBS), collagen colitis and coeliac disease are recruited at the Section of Gastroenterology at the University Hospital of Uppsala. The number of individuals in the different diagnostic groups and sex and age range are given in Table 4. Diagnosis of UC is based on clinical and endoscopic criteria and x-ray of the gut. The histological grading of mucosal activity is based on a grading by Binder and slightly modified and validated by Geboes et al. Individuals with UC had a mean disease duration of 6.3 years (range 1 month to 22 years). Inactive UC is defined as normal macroscopic findings at endoscopy combined with normal blood tests and normal bowel movements. Active UC is diagnosed on the basis of clinical symptoms and when the endoscopic score is 2-4. Five individuals with inactive UC and 7 individuals with active UC had total colitis. The remaining individuals suffer from distal colitis of varying extents. Twenty-one individuals with IBS fulfilled the Romell criteria. Eight of these are diarrhea-predominant, 8 have constipating and 5 have an alternating type of IBS. Individuals with haemorrhoids, rectal fistulas, and anorectal prolapses are excluded as were individuals with ongoing infections or known latex allergy. All healthy individuals included in the study had no gastrointestinal history. All had normal results following a wide number of blood screening tests.

Individuals and individuals are prepared as for routine fibresigmoidoscopy, with a non-irritative hyperosmolar sorbitol rectal enema; 120-240 ml(Klyx; Ferring, Malmö, Sweden) one hour before the test procedure. Nine individuals performed the test without prior preparation because they suffer from active UC.

TABLE 4

Diagnosis, sex, and ages of the individuals and healthy individuals in the study

| Diagnosis | n | Sex(F/M) | Mean age(y) | Age range (y) |
| --- | --- | --- | --- | --- |
| Ulcerative colitis active | 18 | 4/14 | 42.9 | 19-79 |
| Ulcerative colitis inactive | 7 | 3/4 | 49.6 | 26-66 |
| Irritable bowel syndrome, diarrhea-predominant or alternating | 13 | 11/2 | 38.9 | 22-61 |
| Irritable bowel syndrome, Constipation-predominant | 8 | 7/1 | 52.3 | 33-68 |
| Healthy individuals | 15 | 5/10 | 33.5 | 19-58 |

Mucosal Patch Technique

The instrument used for the mucosal patch technique as well positioning of the instrument are as described above. The patches are compressed against the rectal mucosa and used to absorb mediators released to lumen. In summary, the patches are extracted in a solution containing 0.3% CTAB (N-cetyl-N,N,N-trimethyl ammonium bromide; E Merck, Darmstadtr, Germany). The extract with the content is immediately frozen at −70° C. and kept frozen until an analysis in sequence is performed. Blood samples are collected and serum/plasma are frozen at −70° C. until analysed.

Analytical Measurements

Four endogenous opioids are measured using radioimmunoassay; beta-endorphin, endomorphin, met-enkephalin and dynorphin. Corticotropin releasing hormone (CRH) is also analysed by a radioimmunoassay. IL-1 and is measured using Bio-Plex amine coupling kit and analysed with the Bio-plex protein array system (Bio-Rad Laboratories, INC, Hercules, Calif., USA).

Statistics and Calculations

The results are presented as mean+standard error of the mean (SEM) with range in parenthesis. The Mann Whitney U-test, Friedman Anova, sign test and Spearman's sign rank test are used for the statistical calculations.

Results

Mucosal Release of Opioids

FIGS. 2-5 present the luminal release of beta-endorphin, endomorphin, met-enkephalin and dynorphin in individuals with ulcerative colitis, individuals with IBS diarrhea-predominant or alternating type, individuals with IBS and constipation and healthy individuals.

Individuals with active UC have, compared to the healthy individuals, significantly increased release of all opioids measured. Individuals with inactive UC have started to normalize their opioid levels. Individuals with IBS and diarrhea/alternating diarrhea-constipation also show increased release of all opioids and significant increases re noted for met-enkaphalin and dynorphin. Compared with the healthy individuals, individuals with constipation-predominant IBS have similar levels for beta-endorphin, met-enkephalin and dynorphin but somewhat reduced levels for endomorphin compared with the healthy individuals. The opioid release patterns in individuals with coeliac disease (n=6) or collagen colitis (n=9) are quite similar to the release patterns of the healthy individuals (data not shown).

Mucosal Release of Opioids and Histological/Biochemical Assessment of Mucosal Inflammation The relation between the degree of mucosal inflammation in individuals with UC (n=14) and rectal biopsies taken around the time of the present investigation (on average+1.8 days) and the mucosal release of opioids is examined. Met-enkephlin and endomorphin values are significantly correlated (tested by Spearman rank order correlation test) with the overall histological activity (r=0.55 (p<0.05) and r=0.6 (p<0.05), respectively). Endomorphin also correlated (p<0.05) with the numbers of neutrophils in lamina propria (r=0.57) and epithelium (r=0.61), crypt destruction (r=0.55) and ulcerations/erosions (r=0.55). Met-enkephalin is related (p<0.05) to lamina propria eosinophils (r=0.67) and ulcerations (r=0.47). Beta-endorphin correlated (p<0.05) only with ulcerations/erosions (r=0.57).

The mucosal release of the pro-inflammatory cytokine IL-1 is below the detectable levels (<2 ng/L) in healthy individuals and individuals with IBS. Individuals with active UC have a considerably increased release of IL-1 and on average 109+44 ng /L (p<001 compared to healthy individuals as tested by Mann-Whitney U test). Individuals with inactive UC had also measurable IL-1 levels (6.5+3.0 ng /L). Il-1 correlates with endomorphin in the UC group (Table 5).

A mucosal release of CRH, a pro-inflammatory neuropeptide, is apparent in healthy individuals (1.58+0.07 ug L) and of same magnitude as seen in individuals with collagen colitis (1.53+0.07 ng/L) and coeliac disease (1.50+0.06 ng/L). The release of CRH varied within a wide range in individuals with UC and is not related to the disease activity. The median CRH level is 2.41 ug/L (range 1.69-8.24) in active UC (p<0.001) and 4.08 ug/L (range 1.17-15.95) in inactive UC. In UC individuals CRH release is correlated with met-enkephalin and dynorphin (Table 5). The CRH release in constipation-predominant IBS individuals is normal with small variations (1.43+0.08 ug /L) while individuals with diarrhoea-predominant or alternating IBS had significantly increased (p<0.001) and as in UC highly varying values; median value is 5.94 ug/L(range 1.46-26.08). The CRH release correlated with the release of beta-endomorphin, met-enkephalin dynorphin (Table 6).

TABLE 5

Correlations between rectal mucosal release of endogenous opioids and IL1/CRH in individuals with ulcerative colitis

|  | IL-1 r | CRH r |
| --- | --- | --- |
| Endomorphin | 0.58** | ns |
| Beta-endorphin | 0.43* | ns |
| Met-enkephalin | ns | 0.51* |
| Dynorphin | ns | 0.64** |

Correlation coefficients (r) were calculated by Spearman rank order correlation test;
*p < 0.05,
**p < 0.01

TABLE 6

Correlations between rectal mucosal release of endogenous opioids and IL-1/CRH in individuals with IBS of diarrhea predominant or alternating types

|  | IL-1 r | CRH r |
| --- | --- | --- |
| Endomorphin | ns | 0.61* |
| Beta-endorphin | ns | 0.79** |

TABLE 6-continued

Correlations between rectal mucosal release of endogenous opioids and IL-1/CRH in individuals with IBS of diarrhea predominant or alternating types

|  | IL-1 r | CRH r |
| --- | --- | --- |
| Met-enkephalin | ns | 0.55* |
| Dynorphin | ns | 0.60* |

Correlation coefficients (r) were calculated by Spearman rank order correlation test,
**p < 0.01

Discussion

The finding in this example that luminal secretion of endomorphin, beta-endorphin, dynorphin and met-enkephalin is measurable in diseased and healthy rectum is novel and provides possibilities to easily perform clinical studies with regard to the role endogenous opiods may play in inflammatory and functional gastrointestinal disorders. The observation that individuals with diarrhoea-predominant IBS shared a similar increase of the luminal opioid secretion as individuals with UC is intriguing and suggests a pathophysiological link between these conditions.

Ulcerative colitis is a classical chronic inflammatory disease with prominent activation of immunocytes such as neutrophils and macrophages. The symptoms and the mucosal inflammation respond in an excellent way to glucocorticoid treatment. In contrast, lack of efficacy of corticosteroids is observed in IBS which might support the absence of inflammatory components in this common disease. However, the dogma that IBS is characterized by no abnormality of mucosal structure has recently been challenged by demonstrating low-grade lymphocytic infiltration in the gut mucosa, increased permeability and increases in mucosal content of various inflammatory mediators. Furthermore, infectious gastroenteritis may induce IBS.

Endogenous opioid peptides are located in specific sites of the brain, the spinal cord, the autonomic ganglia and the enteric nervous system. Representatives of the various classes of endogenous opioids; beta-endorphin, endomorphin, met-enkephalin and dynorphin studied in the present study are bound to specific receptors; mu delta and kappa receptors, with varying affinity. At the periphery the opioids interact with these receptors present on peripheral sensory nerves resulting in potent analgesia. Individuals with IBS show several clinical and experimental findings suggesting of enhanced sensitivity to certain types of visceral stimulation. Alterations in activation of pain modulating systems have been postulated to play a role in syndromes characterized by discomfort and pain but without detectable structural abnormalities. The abdominal pain and discomfort in IBS has been suggested to be due to either enhanced activation of fasciliatory systems and/or from inadequate activation of pain inhibitory systems. These results suggest that IBS individuals have an increased synthesis of mucosal opioids, which may reflect an endogenous functional way to reduce the abdominal pain. Opioids are able to inhibit nociception arising from inflamed tissue where opioid peptides are released locally from immunocytes taking part in the inflammatory reaction. The inflammatory reaction induces also activation of pain receptors. The finding of enhanced luminal secretion of opioids in UC is compatible with this inflammatory scenario and might reflect an attempt of the body to reduce the abdominal pain. Diarrhea is another symptom seen in UC and subgroups of individuals with IBS. Endogenous opioids also participate by peripheral action in several motor functions and reduce gut motility. Opioids increase Na and Cl absorption and inhibit Cl secretion. Thus, an enhanced luminal secretion of opioids might reflect an adapted mechanism to maintain homeostasis by reducing diarrhea.

Opioid peptides such as endorphin, endomorphin, met-enkephalin and dynorphin can be produced by immune cells in the inflamed tissue. The above findings that the mucosal release of all these opioids are increased in active UC but started to normalize after clinical remission is compatible with the idea that the intensity of the local inflammation directs the local opioid release. The luminal release of the proinflammatory cytokines Il-1 is considerable in active UC but statistical relationships are only seen between the mucosal release of these cytokines and endomorphin and endorphin. Earlier studies have in fact demonstrated that IL-1 is a secretagogue of endorphin but not of enkephalin. Other mechanisms may regulate the release of dynorphin and met-enkephalin, which are mutually related. Mediators behind enhanced mucosal opioid release in IBS are unknown but are not likely to involve pro-inflammatory cytokines like IL-1. It is true that increased interleukin-1 (beta) MRNA expression have been detected in rectosigmoideal biopsies from IBS individuals with an infectious origin. However, only a minority of the IBS individuals in the present study with diarrhea prominent IBS had a history of symptoms developing after infection. Furthermore, significant luminal secretion of Il-1 in the IBS individuals are not detected. Thus, other mediators than IL-1 should be involved in the increased mucosal release of opioids in IBS.

Corticotropin-releasing factor, also known as corticotropin-releasing hormone (CRH), was characterized in 1981 as a novel 41-amino-acid produced in certain neurons of the paraventricular nucleus. CRH is the primary hypothalamic regulatory hormone and of critical importance for the hypothlamic-pituitary-adrenal axis. Significant amounts of immunoreactive CRH are also found in inflamed tissue and released at the site of inflammation by nerve terminals and immunocytes and acts locally by a paracrine action. The local activities of CRH include triggering of the release of opioid peptides from immune cells in vitro and in vivo. The inventor has found high mucosal concentrations of CRH in individuals with UC but have found no correlation to histological or biochemical estimates of mucosal inflammation. In fact, individuals with UC in remission have higher CRH concentrations than individuals with active disease. A significant relationship is seen between the CRH release and the mucosal concentrations of dynorphin and met-enkephalin but not of endorphin/endomorphin. Previous in vitro studies have reported that enkephalin is liberated by CRH and not by IL-1. Thus, while Il-1 seems to direct endomorphin release in UC, CRH may play such a role for the release of met-enkephalin peptide and dynorphin.

An increased luminal secretion of CRH has been found in individuals with diarrhoea-predominant IBS. While not wishing to be bound by theory, it is reasonable to attribute this increase not to a possible subclinical mucosal inflammation but rather to a non-inflammatory stress stimulus. The significant correlations observed in these individuals between their mucosal concentrations of CRH and all measured endogenous opiods suggest that CRH is a central director of opioid release in diarrhea-pre-dominant IBS. Recently, attention has been directed to the possible role of CRH for the symptomatology in IBS. Two major G protein coupled receptors for CRH have been identified, CRH receptor 1 (CRH-R1) and receptor 2 (CRH-R2). In experimental animals, activation of CRH-R1 has been related to stress-induced activation of colonic motility, induction of watery diarrhea and hypersensitivity to colonic distension. Administration of CRH in healthy subjects and individuals with IBS induced increased colonic motility and visceral perception, the major events in the pathophysiology of IBS. Treatment with CRH-receptor antagonist have also been tried with intriguing positive effects on symptoms probably due to peripheral activity since not only immunoreactive CRH but alsoCRH-R1 MRNA have been detected in human colonic mucosa. Thus, it is possible that the observed increased release of mucosal CRH may have a stimulatory effect on the CRH receptors and thereby contribute to the common symptomatology seen in UC and IBS but possible down-regulation of the receptors due to overload of locally released CRH has to be considered. However, the complexity of possible effector results is illustrated by the observations that activation of CRH-R2 prevented visceral sensitisation. Nevertheless, accumulated data are exciting and suggest that future drug development in IBS has to consider various possible strategies with regard to interference with either the release of CRH or the CRH-receptors.

CRH as well as locally produced endogenous opioids are also modulating the inflammatory reaction. CRH present in peripheral tissues seems to have a pro-inflammatory autocrine/paracrine role by causing peripheral vasodilatation and increased vascular permeability and stimulating the activation of immune cells including the secretion of pro-inflammatory cytokines like Il. Furthermore, the experience with specific CRH-R1 receptor agonists or antagonists has clearly demonstrated its proinflammatory role also in vivo. However, activation of CRH-R2 provokes anti-inflammatory changes. In contrast to CRH, locally produced endogenous opioids and in particular beta-endorphin have anti-inflammatory properties by modulating e.g. splenocyte proliferation and production of inflammatory and immunoregulatory cytokines. Beta-endorphin mediates these effects by activating the mu receptor (MOR). Recently it has been reported that selective MOR agonists significantly reduce inflammation in two experimental models of colitis. Since MOR agonists combine analgesic functions, inhibition of intestinal motility and anti-inflammatory effects, it seems beneficial to have a stimulated release of endogenous opioids in the diseased gut in UC as well as in IBS provided that the expression of MOR is not down-regulated. MOR, normally abundant in the myenteric and submucosal plexus, is in fact upregulated in human IBD mucosa and mainly in inflammatory mononuclear cells.

The role of locally produced proinflammatory CRH seems to be a central component for the enhancement of the mucosal inflammatory reaction. The biological effects of increased release of CRH in functional non-inflammatory disease like IBS are uncertain. It may certainly influence the colonic motility by increasing the colonic intraluminal pressure. The apparent lack of mucosal inflammation and the absence of detectable IL-1 release in the IBS individuals in spite of large amounts of proinflammatory CRH might seem conflicting. However, the findings are compatible with a minimal effect by CRH on cytokine production by unstimulated immunocytes. It is possible that the discrete inflammatory signals reported in the IBS mucosa might reflect a local CRH effect. It is also reasonable to assume that the increased mucosal CRH release in IBS is not a secondary event to inflammation but could rather reflect a non-inflammatory stress stimulus enhancing a neuronal origin. One may also speculate that an increased basal mucosal synthesis of CRH in IBS might prime the mucosa to inflammatory reactions induced by e.g., an infectious agent.

The observations of increased mucosal release of endogenous opioids and CRH in IBS offer more data on the complexity of IBS and emphasize the links between this syndrome and UC. Furthermore, an objective method of potential clinical importance in the diagnosis and therapeutic follow-up studies of individuals with especially IBS, a disease which has been awaiting easily available biological markers, is provided.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A method for measuring at least one neuroendocrine gut system component in an individual, comprising: measuring at least one neuroendocrine gut system component released in vivo from mucosa of the individual, wherein the measuring occurs without having to remove mucosa from the body of the individual.

2. The method of claim 1, wherein the measurement comprises measuring at least one neuroendocrine gut system component released from a lumen of the colon, the rectum or a combination thereof of the individual.

3. The method of claim 1, wherein the measurement of the neuroendocrine gut system component comprises conducting mucosal patch technique, perfusion of the colon and/or rectum, dialysis of the colon and/or rectum, analysis of fecal content, or a combination thereof.

4. The method of claim 1, wherein the neuroendocrine gut system component comprises a neurohormone, a neuropeptide, an endogenous opiod, a neurotransmitter or a combination thereof.

5. A method for diagnosing a gastrointestinal disorder in an individual, comprising: measuring at least one neuroendocrine gut system component released in vivo from mucosa of the individual, wherein the measuring occurs without having to remove mucosa from the body of the individual, calculating the concentration of the at least one neuroendocrine gut system component, and diagnosing the gastrointestinal disorder in the individual by comparing the concentration of the at least one neuroendocrine gut system component with a predetermined concentration of the at least one neuroendocrine gut system component indicative of the gastrointestinal disorder.

6. The method of claim 5, wherein the gastrointestinal disorder comprises an inflammatory gastrointestinal disorder, a functional gastrointestinal disorder, or a combination of gastrointestinal disorders.

7. The method of claim 6, wherein the inflammatory gastrointestinal disorder comprises ulcerative colitis, Crohn's disease or a combination thereof.

8. The method of claim 6, wherein the functional gastrointestinal disorder is irritable bowel disease.

9. The method of claim 5, wherein the measurement comprises measuring at least one neuroendocrine gut system component released from a lumen of the colon, the rectum or a combination thereof of the individual.

10. The method of claim 5, wherein the measurement of the neuroendocrine gut system component comprises conducting mucosal patch technique, perfusion of the colon and/or rectum, dialysis of the colon and/or rectum, analysis of fecal content, or a combination thereof.

11. The method of claim 5, wherein the neuroendocrine gut system component comprises a neurohormone, a neuropeptide, an endogenous opiod, a neurotransmitter or a combination thereof.

12. The method of claim 11, wherein the neurohormone comprises chromogranin A, chromogranin B or a combination thereof.

13. The method of claim 11, wherein the neuropeptide comprises Corticotropin Releasing Hormone (CRH), Substance P, Peptide YY (PYY), Vasoactive Intestinal Peptide (VIP), or a combination thereof.

14. The method of claim 11, wherein the neurotransmitter comprises serotonin, adrenalin, non-adrenaline or a combination thereof.

15. The method of claim 5, wherein the neuroendocrine gut system component comprises Corticotropin Releasing Hormone (CRH) and the predetermined concentration indicative of the gastrointestinal disorder is above 2 ug/L.

16. A method for diagnosing a gastrointestinal disorder in an individual, comprising: measuring at least one neuroendocrine gut system component and at least one release inflammatory mediator of the individual, calculating the concentrations of the at least one neuroendocrine gut system component and the at least one release inflammatory mediator, determining a ratio of the concentrations of the at least one neuroendocrine gut system component and the at least one release inflammatory mediator, and diagnosing the gastrointestinal disorder in the individual by comparing the ratio of the concentrations of the at least one neuroendocrine gut system component and the least one release inflammatory mediator with a predetermined ratio of the concentrations of the at least one neuroendocrine gut system component and the at least one release inflammatory mediator indicative of the gastrointestinal disorder, wherein the at least one neuroendocrine gut system component and/or the at least one release inflammatory mediator are released in vivo from mucosa of the individual, and the measuring occurs without having to remove mucosa from the body of the individual.

17. The method of claim 16, wherein the measurement of the neuroendocrine gut system component comprises conducting mucosal patch technique, perfusion of the colon and/or rectum, dialysis of the colon and/or rectum, analysis of fecal content, or a combination thereof and wherein the measurement of the release inflammatory mediator comprises conducting mucosal patch technique, perfusion of the colon and/or rectum, dialysis of the colon and/or rectum, analysis of fecal content, or a combination thereof.

18. The method of claim 16, wherein the neuroendocrine gut system component comprises a neurohormone, a neuropeptide, an endogenous opiod, a neurotransmitter or a combination thereof.

19. The method of claim 18, wherein the neurohormone comprises chromogranin A, chromogranin B or a combination thereof.

20. The method of claim 18, wherein the neuropeptide comprises Corticotropin Releasing Hormone (CRH), Substance P, Peptide YY (PYY), Vasoactive Intestinal Peptide (VIP), or a combination thereof.

21. The method of claim 18, wherein the neurotransmitter comprises serotonin, adrenalin, non-adrenaline or a combination thereof.

22. The method of claim 16, wherein the inflammatory mediator comprises proinflammatory cytokine, granule constituents from macrophages, granulocytes or basophils/mast cells or a combination thereof.

23. The method of claim 16, wherein the ratio comprises a ratio of Corticotropin Releasing Hormone (CRH): Interleukin-6(IL-6) or a ratio of Chromogranin A (CgA): Myeloperoxidase (MPO).

24. The method of claim 16, wherein at least one neuroendocrine gut system component which is measured is released from mucosa of the individual.

* * * * *